United States Patent [19]

Oka et al.

[11] Patent Number: 5,214,288
[45] Date of Patent: May 25, 1993

[54] METHOD AND APPARATUS FOR TWO-DIMENSIONAL MEASUREMENT OF CONCENTRATION OF BIOLOGICAL MACROMOLECULE SOLUTION

[75] Inventors: Kotaro Oka; Koji Asano; Shozo Fujita, all of Kawasaki, Japan

[73] Assignee: Fujitsu Limited, Kawasaki, Japan

[21] Appl. No.: 809,123

[22] Filed: Dec. 18, 1991

[30] Foreign Application Priority Data

Dec. 18, 1990 [JP] Japan .................. 2-403315

[51] Int. Cl.$^5$ .................. G01J 1/42; G01N 21/33
[52] U.S. Cl. .................. 250/373; 250/372
[58] Field of Search .................. 250/373, 372

[56] References Cited

U.S. PATENT DOCUMENTS

| | | | |
|---|---|---|---|
| 3,751,167 | 8/1973 | Claus .................. | 250/373 |
| 4,192,996 | 3/1980 | Kronick et al. .................. | 250/373 |
| 4,207,892 | 6/1980 | Binder .................. | 250/373 |
| 4,587,428 | 5/1986 | Binder .................. | 250/372 |
| 4,919,899 | 4/1990 | Herrmann et al. .................. | 422/245 |

FOREIGN PATENT DOCUMENTS

| | | |
|---|---|---|
| 0080699 | 6/1983 | European Pat. Off. . |
| 0225050 | 6/1987 | European Pat. Off. . |
| 0380904 | 8/1990 | European Pat. Off. . |

OTHER PUBLICATIONS

P. J. Shlichta, "Feasibility of Mapping Solution Properties During the Growth of Protein Crystals," Journal of Crystal Growth, vol. 76, No. 3, Aug. 1986, Amsterdam, NL, pp. 656–662.

*Primary Examiner*—Carolyn E. Fields
*Assistant Examiner*—Drew A. Dunn
*Attorney, Agent, or Firm*—Staas & Halsey

[57] ABSTRACT

A method of making a two-dimensional measurement of the concentration of a biological macromolecule aqueous solution and an apparatus for carrying out this method are disclosed. By charging the biological macromolecule aqueous solution and an aqueous crystallizing agent solution into a crystallizing cell, irradiating the crystallizing cell with an ultraviolet light from an ultraviolet light source, two-dimensionally scanning the ultraviolet light transmitted through the crystallizing cell by a linear image sensor to detect the quantity of the transmitted light, and carrying out a conversion of the detected quantity of the transmitted light to the protein concentration, the process of a crystallization of the biological macromolecule from biological macromolecule aqueous solution can be easily and accurately twodimensionally measured.

15 Claims, 4 Drawing Sheets

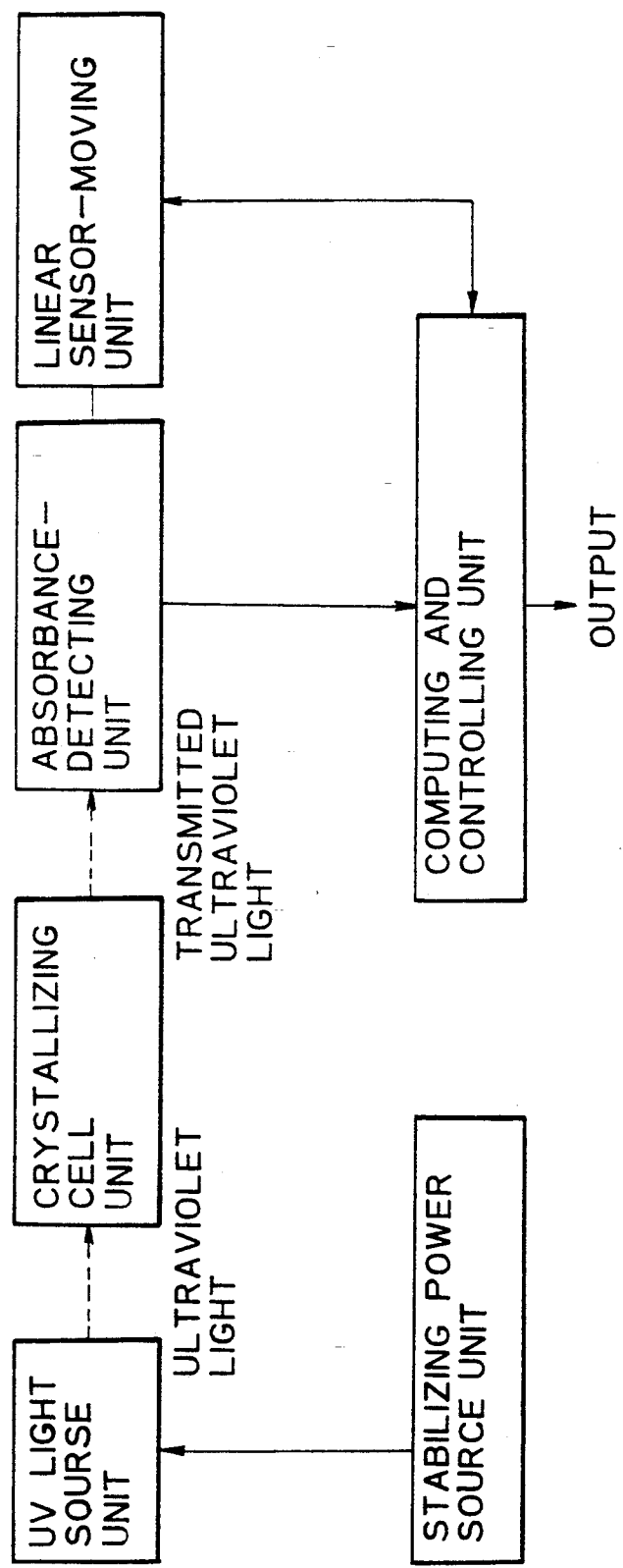

METHOD AND APPARATUS FOR TWO-DIMENSIONAL MEASUREMENT OF CONCENTRATION OF BIOLOGICAL MACROMOLECULE SOLUTION

BACKGROUND OF THE INVENTION

1. Filed of the Invention

The present invention relates to a method of making a two-dimensional measurement of the concentration of a biological macromolecule solution, and an apparatus for use when carrying out this method. More particularly, the present invention relates to a method of observing the process of crystallization of a biological macromolecule, and an apparatus for two-dimensionally scanning the process of crystallization of the biological macromolecule when carrying out this method.

2. Description of the Related Art

Biological macromolecules such as proteins, polypeptides and nucleic acids exert important functions such as energy metabolism, structure construction and information transmission, and it is known that these functions of biological macromolecules result from the structures thereof, and therefore, the need for an investigation of the three-dimensional structure of a biological macromolecule has increased. As a method of analyzing this three-dimensional structure of the biological macromolecule, in general the NMR (nuclear magnetic resonance) method, the X-ray diffraction method, and the like are adopted, although the X-ray diffraction method is now attracting attention because it enables the three-dimensional structure to be directly analyzed.

To accomplish the X-ray diffractometry, it is important that a biological macromolecule crystal having a structure reduced disorder and a high quality be obtained, but it is difficult to obtain a high-quality crystal of a biological macromolecule because the crystallization conditions differ according to respective biological macromolecules, and the optimum conditions must be determined by trial and error. Furthermore, since knowledge about the growth process conditions of crystal nuclei of biological macromolecule crystals is limited, it is difficult to obtain a biological macromolecule crystal having a high quality.

Recently, trials have been initiated to examine in detail the growth process of a crystal of a biological macromolecule, especially a protein (see, for example, Azuma et al., J. Crystal Growth, 98, 371–376, 1989). In this thesis, the process of crystallization of a protein is traced by measuring changes of the refractive index in the vicinity of the crystal, by utilizing a Mach-Zehender interference optical system. According to this method, it becomes possible to perform a two-dimensional measurement of the concentration gradient in the diffusion foundary layer around a growing crystal as a function of concentration of the lysozyme concentration, but the method of measuring the protein concentration by the differential interference optical system has several problems. First, since the protein concentration is measured, based on the refractive index, there is a risk of mistaking a change of the solute concentration in a crystal mother liquor for a change of the protein concentration, and second, since for a conversion of the refractive index to the protein concentration it is necessary to measure the space between interference fringes in the vicinity of the crystal and the mother liquor having a concentration gradient in the diffusion boundary layer around a growing crystal interface, a complicated operation such as image processing is necessary by transforming the refractive index gradient using the Lorentz-Lorentz formula.

A two-dimensional measuring apparatus utilizing ultraviolet rays recently has been developed as an analysis and measurement apparatus. As the two-dimensional measurement apparatus utilizing ultraviolet rays, there can be mentioned, for example, an ultraviolet microscope. An apparatus is known which is constructed by combining this ultraviolet microscope with a microscope photometer (MPM) system, so that the intercellular calcium concentration and the DNA quantity can be measured. For example, there can be mentioned the MPM System supplied by Carl Travis Co. This apparatus, however, is not designed for the analysis of a biological macromolecule crystal, and it has to comprise a heavy, large, and delicate specific optical system. Thus, although a point light measurement by a microscope system can be performed, it is not possible to promptly perform a light measurement over a wide range.

Accordingly, the development of a method of two-dimensionally tracing the crystallization process of a biological macromolecule, easily and promptly, and of measuring the concentration of a biological macromolecule concentration, and a simple and small apparatus for carrying out this method, is desired.

SUMMARY OF THE INVENTION

The present invention has been completed as the result of research made with a view to solving the foregoing problems, and an object of the present invention is to provide a method of two-dimensionally scanning the concentration of a biological macromolecule in a biological macromolecure aqueous solution, more specifically the crystallization process of a biological acromolecules from biological macromolecule, such as myoglobin, aqueous solution, and a simple apparatus for carrying out this method.

In accordance with one aspect of the present invention, there is provided a method of making a two-dimensional measurement of the concentration of a biological macromolecule aqueous solution, which comprises charging the biological macromolecule aqueous solution and a crystallizing agent aqueous solution into a crystallizing cell, irradiating the crystallizing cell with an ultraviolet light from an ultraviolet light source and two-dimensionally scanning the ultraviolet light transmitted through the crystallizing cell by a linear sensor, to detect the quantity of the transmitted light, and converting the detected quantity of transmitted light to the biological macromolecule concentration in the biological macromolecule solution.

In accordance with another aspect of the present invention, there is provided an apparatus for the two-dimensional measurement of the concentration of a biological macromolecule solution, which comprises an ultraviolet light source unit, a crystallizing cell, an absorbance-detecting unit, and a computing and controlling unit for a substraction or differentiation of the quantity of the light transmitted from the absorbance-detecting unit, wherein the ultraviolet light source unit, the crystallizing cell, and the absorbance-detecting unit are arranged in the recited order.

Any conventional linear image sensor may be employed in accordance with the present invention, and the same is referred to herein by various different but equivalent terms, such as a "one-dimensionally arranged photodiode", and "observance-detecting unit", a "linear sensor-moving unit" and a "primary scanning sensor", which equivalent terms further characterize the structure and functional purpose of the sensor device.

Other features, objects, and advantages of the present invention will become apparent from the following detailed description made with reference to the accompanying drawings.

BRIEF DESCRIPTION OF THE DRAWINGS

FIG. 1 illustrates the structure of the apparatus of the present invention;

DESCRIPTION OF THE PREFERRED EMBODIMENTS

Figure 2A:
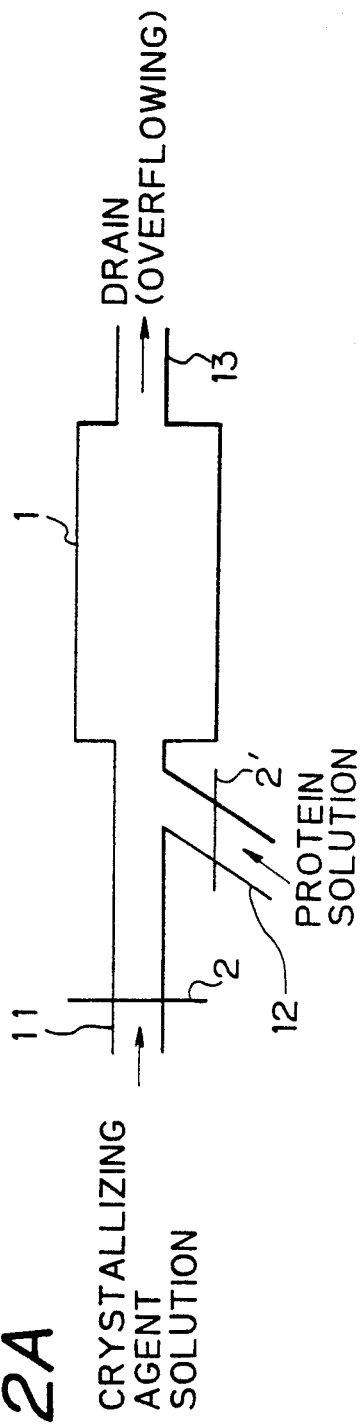
FIG. 2(A) illustrates a protein-crystallizing cell used in the free interface method.

In the present invention, it has been noted that many biological macromolecules show peculiar absorbances of light in the ultraviolet ray region, and thus the present method and apparatus are constructed so that a two-dimensional scanning of the ultraviolet light absorbance by detecting the light transmitted through the cell can be accomplished. Therefore, the measurement of the process of growth of a protein crystal, more specifically the protein concentration, can be performed two-dimensionally.

The subject of the measurement in the present invention includes proteins and nucleic acids.

An inorganic salt such as a neutral salt or an organic compound such as an alcohol is preferably used as the crystallizing agent. For example, inorganic salts such as ammonium sulfate, NaCl, KCl, sodium sulfate, a phosphate and cesium chloride are preferably used, and organic compounds such as polyethylene glycol, water-miscible solvents (for example, methanol and ethanol), dioxane and methylpentane-diol are preferably used.

The present invention will now be described in detail with reference to the following examples, which by no means limit the scope of the invention.

EXAMPLE 1

FIG. 1 illustrates a block diagram of the structure of the apparatus of the invention. As seen from this structural diagram, the apparatus of the present invention comprises a light source unit capable of uniformly irradiating a measurement range with a specific ultraviolet light for example 280nm or 254nm, a cell for carrying out crystallization, a detecting unit (absorbance-detecting unit) for measuring a change of the protein concentration, caused by nucleous formation and/or crystal growth, and a computing and controlling unit for converting the output of the detecting unit to a measurement of the concentration of a biological macromolecule. A linear image sensor-moving or driving unit is connected to the absorbance-detecting unit, as described below, to co-operate with the computing and controlling unit.

The ultraviolet light source unit comprise an ultraviolet light source and a spectral element. For example, a deuterium discharge tube and a low-pressure mercury lamp are used as the light source. This low-pressure mercury lamp has a long life of about 10,000 hours. The spectral element comprises, for example, a monochromator or an interference filter. A stabilizing power source unit is connected to the ultraviolet light source unit, to maintain the voltage at a constant level. The stabilizing power source device can be fabricated by utilizing a known fluorescent lamp-lighting circuit.

An ultraviolet light having a specific wavelength necessary for the measurement of the concentration is obtained in the following manner. Namely, a light having a wavelength of about 280 nm (wavelength specific to a protein) is obtained by using phosphor and an interference filter, and an emission line having a wavelength of 254 nm, generated by a low-pressure mercury lamp, is used as the light having a wavelength of 260 nn (wavelength specific to a nucleic acid). An ultraviolet light-transmitting face (4 mm × 10 mm) of a crystallizing cell described below is uniformly irradiated with the above-mentioned light source device.

Figure 2B:
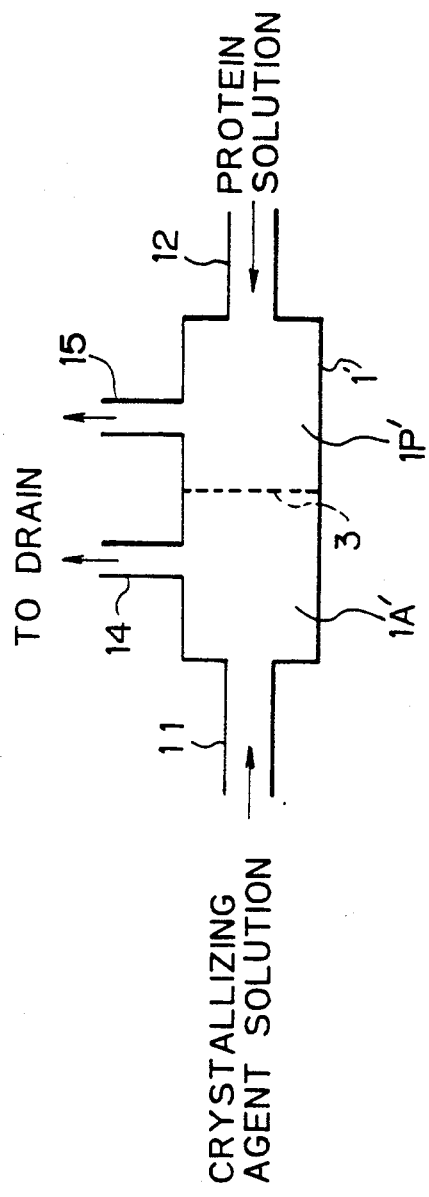
FIG. 2(B) illustrates a protein-crystallizing cell used in the dialysis diffusion method.

The protein-crystallizing cell is designed to be used for the free interface method and the dialysis diffusion method, having a different crystal growth system (see FIGS. 2A and 2B, respectively).

FIG. 2(A) illustrates a protein-crystallizing cell used for the free interface method, and FIG. 2(B) illustrates a protein-crystallizing cell used for the dialysis diffusion method.

According to the free interface method, a liquid-liquid interface is formed between the aqueous solution of the crystallizing agent and the aqueous solution of the protein, to form a concentration gradient. In this method, branches 11, 12 are arranged in relation to the crystallizing cell 1, as shown in FIG. 2(A), to independently introduce the aqueous crystallizing agent solution and the aqueous protein solution within the crystallizing cell 1, and a partition plate 2, 2' is attached to each branch 11, 12. One end of the cell 1 is opened to discharge the overflowing solution through a drain 13. According to this method, the partition plate 2 is opened to fill the aqueous crystallizing agent solution into the cell 1 through a conduit 11 arranged on one end of the crystallizing cell 1, and the partition plate 2 is then closed and the partition plate 2' is opened to charge the aqueous protein solution into the cell 1 through the branch 12. When the liquid-liquid interface of the crystallizing agent solution and the protein solution is located almost at the center of the cell 1, the partition plate 2' is then closed. The crystallizing agent solution overflowing during this operation is discharged from the drain tube 13.

Figure 3:
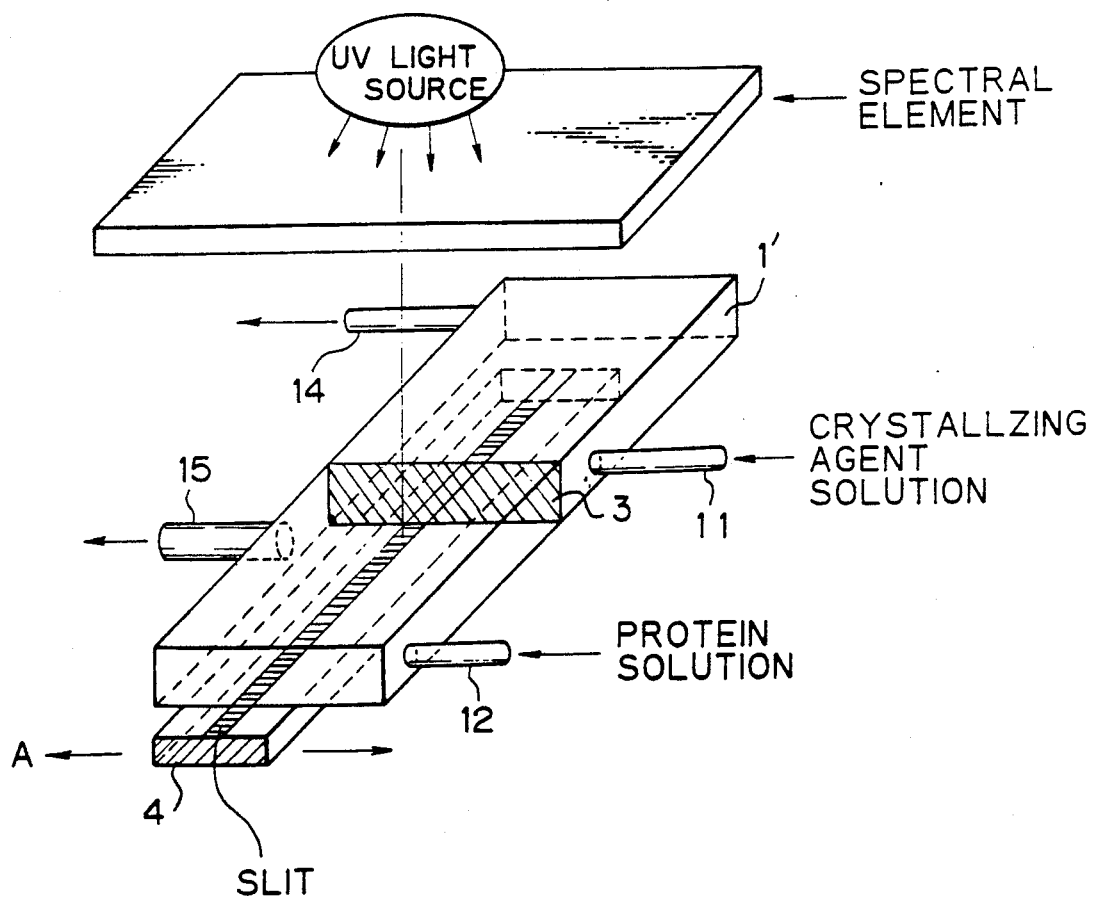
FIG. 3 is a perspective view of a main part of one embodiment of the present invention; and, FIG. 4 illustrates the point of measuring the width of a quartz cell.

According to the dialysis diffusion method as shown in FIG. 2B a gradient of the concentration is formed between at the opposite sides of the membrane 3. In this method, as shown in FIG. 2(B), the permeable membrane 3 is attached at almost the center of the crystallizing cell 1'. The pore size of the permeable membrane 3 is such that the passage of the crystallizing agent is allowed but the passage of the protein is not allowed. The interior of the cell 1'. divided into two chambers 1P', 1A' by this permeable membrane 3. Branch 12 at one end of the cell is opened to introduce the protein solution into one chamber 1P', and furthermore, an opening 15 for discharging the overflowing solution is formed. Branch 11 at the other end of the cell 1' is opened to introduce the crystallizing agent solution into the other chamber 1A', and furthermore, an opening 14 is formed to discharge the overflowing solution [see FIG. 2(B) and FIG. 3]. According to this method, for example, the experiment can be carried out while simultaneously introducing the crystallizing agent solution and the into the cell 1'.

In each of the foregoing methods, a gradient of the protein concentration is formed in the vicinity of the liquid-liquid free interface region or the permeable membrane, and by procedures described below, the point of the concentration gradient where a crystal of the protein is first formed is determined.

Obviously, a method other than the above-mentioned methods, such as a stationary batchwise method, can be similarly adopted.

In the present example, a quartz glass is used as the material of the cell for measuring the ultraviolet light absorbance. In view of the used protein concentration (ordinarily 1 to 5 mg/ml), the cell thickness (optical path length) is adjusted to 2 mm. In view of the size of a primary scanning sensor, the length and width of the crystallizing cell are adjusted to 10 mm and 4 mm respectively. Because of poor processability of the quartz glass, a rectangular parallelopiped shape is adopted for the cell. In the present invention, the amounts used of the protein solution and the crystallizing agent solution are preferably 0.3 ml and 1.5 ml, respectively, in the dialysis diffusion method, and each of the respective amounts of both solutions is preferably 0.3 ml in the dialysis diffusion method.

A high ultraviolet ray spectral sensitivity and a good space resolving power are required for the absorbance-detecting unit. Accordingly, a linear image sensor (for example, S3923-1024Q supplied by Hamamatsu Photonics) is used as the element 4 in FIG. 3 and as the "absorbance-detecting unit" referred to hereinabove and also as the "linear sensor-moving unit" element of FIG. 1. This sensor can scan a range of 25.6 mm at a resolving power of 25 $\mu$m. A drive circuit C4704 for the MOS Linear Image Sensor and a Pulse Generator C4091, each supplied by Hamamatsu Photonics, are used as the drive circuit. The output is supplied to a storage oscilloscope. To scan a two-dimensional region of 4 mm×10 mm by the linear image sensor, it is necessary to move the linear image sensor at a pitch of 25 $\mu$m, and thus a mechanical stage for a microscope (not shown) is used. By using this apparatus, a region of 4 mm×10 mm can be scanned at a pitch of 25 $\mu$m (see FIG. 3).

The computing and controlling unit performs the control of the movement of the linear image sensor by controlling and driving the mechanical stage and the computation of the output from the ultraviolet ray-detecting portion. The computation in the ultraviolet ray-detecting portion is a differentiation or subtraction between the output signal of the empty crystallizing cell and the output signal of the cell at the measurement step. By this computation, the irradiation intensity unevenness can be eliminated. Furthermore, in this computing unit, the conversion of the absorbance to the concentration can be performed.

EXAMPLE 2

In the present example, the method of measuring the protein concentration of the protein aqueous solution by using protein myoglobin is illustrated. The experiment is carried out according to the free interface method wherein an aqueous ammonium sulfate solution (97% saturation) as the crystallizing agent and a 1.0% myoglobin aqueous solution (dissolved in 55% saturation ammonium sulfate aqueous solution) are independently charged in syringes, are connected through a three-way cock, and are put into a quartz glass cell [see FIG. 2(A)] in sequence, whereby a liquid-liquid interface is formed between the ammonium sulfate aqueous solution and the myoglobin aqueous solution. The system is kept stationary and the experiment is carried out at room temperature.

Figure 4:
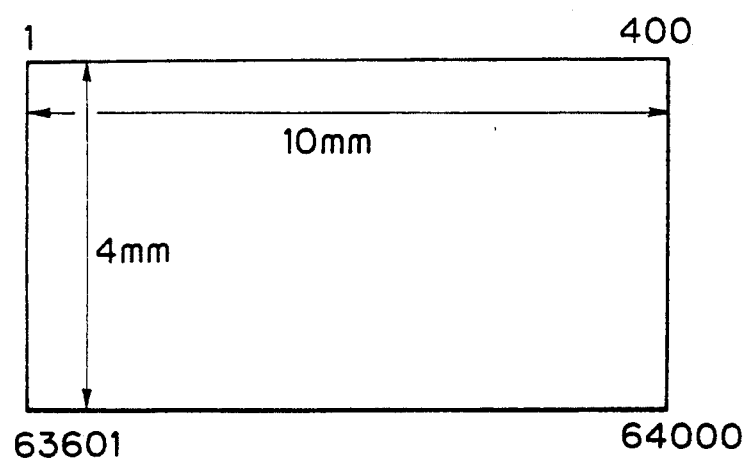

The quantity of the transmitted light of the empty quartz cell is measured just before an injection of the aqueous solutions into the quartz cell, and the linear image sensor is moved intermittently at a pitch of 25 $\mu$m by the mechanical stage. The measurement is conducted over the entire region of 4 mm×10 mm of the quartz cell, to obtain data of 64,000 points. The measurement points in the quartz cell are shown in FIG. 4.

The obtained data is subjected as the quantity of the transmitted light in the empty cell to 16-bit analogdigital (AD) conversion and is stored in a microcomputer. After the start of the experiment, data is obtained at intervals of 2 hours, to trace the crystallization process.

Data obtained at the respective measurement points is accumulated as common logarithms (absorbances A) of the ratio of the data (Io) in the empty cell to the transmitted light quantity (I) at each time. The absorbance can be converted to the molar concentration of the protein according to the following Lambert-Beer equation:

$$\log (Io/I) = A = k \times C \times l$$

wherein k is the molar absorption constant, c represents the molar concentration, and l is the optical path length. More simply, the conversion can be performed by using the formula of protein concentration (mg/ml)=1.45×A. The value of 1.45 in the above-mentioned formula is the constant for converting the absorbance to the concentration expressed in the units of mg/ml.

The values of the absorbance obtained after an elapsd intervals of 24 hours and 48 hours from the point of the start of the experiment are shown in Tables 1 and 2 respectively. The value (4250) given at the corner of each of Tables 1 and indicates the left-upper measurement point, and a symbol "*" indicates a out-of-scale value.

TABLE 1

| Absorbance after 24 Hours from Start of Experiment | | | | | | | | |
|---|---|---|---|---|---|---|---|---|
| 4250 | 4251 | 4252 | 4253 | 4254 | 4255 | 4256 | 4257 | 4258 |
| .68 | .70 | .75 | .88 | .90 | .89 | .80 | .50 | .44 |
| .68 | .69 | .77 | 1.01 | .98 | .90 | .88 | .60 | .46 |
| .68 | .68 | .89 | * | 1.05 | .99 | .97 | .56 | .45 |
| .70 | .88 | .99 | 1.00 | * | * | .90 | .75 | .46 |
| .68 | .78 | .97 | 1.12 | 1.06 | .98 | .80 | .77 | .46 |
| .68 | .73 | .85 | .98 | .90 | .89 | .82 | .67 | .45 |
| 6250 | | | | | | | | 6258 |

TABLE 2

| Absorbance after 24 Hours from Start of Experiment | | | | | | | | |
|---|---|---|---|---|---|---|---|---|
| 4250 | 4251 | 4252 | 4253 | 4254 | 4255 | 4256 | 4257 | 4258 |
| .86 | .70 | .75 | .85 | * | * | 1.20 | .89 | .68 |
| .84 | 1.52 | 1.93 | * | * | * | 1.80 | 1.00 | .63 |
| 1.00 | * | .99 | * | * | * | * | .98 | .69 |
| 1.70 | .95 | 1.80 | * | * | * | 1.67 | 1.05 | .75 |
| 1.55 | 1.05 | 1.86 | * | * | 1.83 | 1.33 | .81 | .65 |
| 1.23 | .98 | .85 | .98 | 1.67 | * | .99 | .67 | .68 |
| 6250 | | | | | | | | 6258 |

From the results shown in Table 1, the following can be seen.

The crystallization of myoglobin starts after an elapsed interval of about 24 hours from the initiation of the experiment. The crystallization begins in the form of a band at a position 2 to 3 mm apart from the liquid-liquid interface (see absorbance values at measurement points of 4253 to 4255). The formation of a crystal nucleus in the protein solution is judged from a sharp rise of the absorbance and a out-of-scale value of the absorbance (because the measurement becomes impossible) (see absorbance values at measurement points of 4653, 4654, 4655, 5051, 5053 and 5054 in Table 2). Also, the increase of the protein concentration in the protein solution is observed in the peripheral portion of the crystal nucleus.

The manner of the growth of the crystal nucleus can be confirmed by tracing the number of measurement points occupied by the crystal. In Table 2, it is seen that the crystal nucleus grows at the out-of-scale point.

According to the present invention, due to the above-mentioned structure, various effects as mentioned below can be attained. First, the process of crystallization of a biological macromolecule can be two-dimensionally traced. Note, by using the apparatus of the present invention, the process of crystallization of a biological macromolecule such as a protein can be measured at a space resolving power of 25 $\mu$m and a concentration difference resolving power of 1/100 of the initial concentration within a dynamic range of 5 to 50 mg/ml.

The optical system of the apparatus of the present invention is much simpler than that of the conventional apparatus such as PMP system for measuring the protein concentration, and the size thereof can be reduced and the weight lowered. Therefore, a measurement error caused by a change of the salt concentration, which is a defect of the conventional apparatus, can be completely eliminated. Furthermore, a conversion to the concentration value can be performed more easily than in the conventional apparatus. Still further, the apparatus of the present invention can be applied to various crystallization processes.

We claim:

1. A method of making a two-dimensional measurement of a concentration of a biological macromolecule solution, comprising: charging the biological macromolecule solution and a crystallizing agent solution into a crystallizing cell, irradiating the crystallizing cell with an ultraviolet light from an ultraviolet light source, two-dimensionally scanning the ultraviolet light transmitted through the crystallizing cell by a sensor to detect the quantity of the transmitted light, and carrying out a conversion of the detected quantity of the transmitted light to a measurement of the protein concentration.

2. A measurement method according to claim 1, wherein the biological macromolecule solution is a protein solution.

3. A measurement method according to claim 2, wherein said sensor is operated to measure the absorbance.

4. A measurement method according to claim 1, wherein the sensor which detects the quantity of the transmitted light is a linear image sensor.

5. A measurement method according to claim 4, wherein said sensor is operated to measure the absorbance.

6. A method according to claim 1, wherein the absorbance is calculated from the ratio of the detected quantity of transmitted light of the charged cell of the biological macromolecule solution to the detected quantity of transmitted light of an empty cell, and the absorbance is converted to the biological macromolecule solution.

7. A measurement method according to claim 6, wherein said sensor is operated to measure the absorbance.

8. A measurement method according to claim 1, wherein said sensor is operated to measure the absorbance.

9. A measurement method according to claim 1, wherein the transmitted light quantity is detected with respect to an empty measurement cell and with respect to a picture element, and a differential computation is performed while holding the measurement data.

10. A method according to claim 1, wherein said macromolecule solution is an aqueous biological solution and said crystallizing agent solution is an aqueous crystallizing agent solution.

11. A method according to claim 1, wherein said sensor is a two-dimensional sensor.

12. An apparatus for a two-dimensional measurement of a concentration of a biological macromolecule solution, comprising: an ultraviolet light source unit, a crystallizing cell, an absorbance-detecting unit and a computing and controlling unit which performs a subtraction or differentiation of the quantity of the transmitted light from the absorbance-detecting unit, wherein the ultraviolet light source unit, the crystallizing cell and the absorbance-detecting unit are arranged in the recited order.

13. A two-dimensional measurement apparatus as set forth in claim 12, wherein the ultraviolet light source unit comprises an ultraviolet ray source and a spectral unit.

14. A two-dimensional measurement apparatus as set forth in claim 12, wherein the ultraviolet light source unit is a deuterium discharge tube or a low-pressure mercuay lamp.

15. A two-dimensional measurement apparatus as set forth in claim 12, wherein the spectral unit is a monochromator or an interference filter.

* * * * *

UNITED STATES PATENT AND TRADEMARK OFFICE
CERTIFICATE OF CORRECTION

PATENT NO. : 5,214,288
DATED : May 25, 1993
INVENTOR(S) : Kotaro OKA et al.

It is certified that error appears in the above-indentified patent and that said Letters Patent is hereby corrected as shown below:

On title page
[57] Abstract, last line, change "twodimensionally" to --two-dimensionally--.

Col. 1, line 55, change "foundary" to --boundary--.

Col. 2, line 38, change "acromolecules" to --macromolecule--; and change "macromolecule" to --macromolecules--.

Col. 3, line 67, change "comprise" to --comprises--.

Col. 4, line 61, change "1'," to --1' is--.

Col. 5, line 5, after "the" insert --protein solution--.

Col. 6, line 45, change "a" (second occurrence) to --an--.

Col. 7, line 10, change "a" to --an--.

Col. 8, line 53, change "mercuay" to --mercury--.

Signed and Sealed this

Fifth Day of July, 1994

BRUCE LEHMAN

Attest:

Attesting Officer

Commissioner of Patents and Trademarks